United States Patent
Yanni

(12) 
(10) Patent No.: US 6,375,973 B2
(45) Date of Patent: Apr. 23, 2002

(54) OPHTHALMIC ANTI-ALLERGY COMPOSITIONS SUITABLE FOR USE WITH CONTACT LENSES

(75) Inventor: John M. Yanni, Burleson, TX (US)

(73) Assignee: Alcon Universal Ltd., Hunenberg (CH)

( * ) Notice: Subject to any disclaimer, the term of this patent is extended or adjusted under 35 U.S.C. 154(b) by 0 days.

(21) Appl. No.: 09/768,444

(22) Filed: Jan. 24, 2001

Related U.S. Application Data

(60) Provisional application No. 60/177,804, filed on Jan. 25, 2000.

(51) Int. Cl.$^7$ .................................................. A61F 2/00
(52) U.S. Cl. ........................ 424/427; 424/428; 514/912
(58) Field of Search .............................. 424/78.02, 422

(56) References Cited

U.S. PATENT DOCUMENTS

| | | | |
|---|---|---|---|
| 3,931,319 A | 1/1976 | Green et al. | 260/567.6 |
| 4,027,020 A | 5/1977 | Green et al. | 424/248.56 |
| 4,407,791 A | 10/1983 | Stark | 424/80 |
| 4,430,343 A | 2/1984 | Iemura et al. | 424/250 |
| 4,525,346 A | 6/1985 | Stark | 424/80 |
| 4,836,986 A | 6/1989 | Ogunbiyi et al. | 422/28 |
| 4,871,865 A | 10/1989 | Lever, Jr. et al. | 549/354 |
| 4,923,892 A | 5/1990 | Lever, Jr. et al. | 514/450 |
| 5,037,647 A | 8/1991 | Chowhan et al. | 424/78 |
| 5,116,863 A | 5/1992 | Oshima et al. | 514/450 |
| 5,192,780 A | 3/1993 | York et al. | 514/357 |
| 5,300,287 A | 4/1994 | Park | 424/78.04 |
| 5,342,620 A | 8/1994 | Chowhan | 424/422 |
| 5,441,958 A | 8/1995 | Yanni et al. | 514/253 |
| 5,603,929 A | 2/1997 | Desai et al. | 424/78.04 |
| 5,641,805 A | 6/1997 | Yanni et al. | 514/450 |
| 5,653,972 A | 8/1997 | Desai et al. | 424/78.04 |
| 5,668,133 A | 9/1997 | Yanni et al. | 514/253 |
| 6,146,622 A | * 11/2000 | Castillo et al. | 424/78.02 |

FOREIGN PATENT DOCUMENTS

WO             91/09523        7/1991

OTHER PUBLICATIONS

Ruben et al., "Pilocarpine dispensation for the soft hydrophilic contact lens," *British J. of Ophthalmology*, vol. 59, pp. 455–458 (1975).

Patanol® (olopatadine hydrochloride ophthalmic solution) 0.1% package insert.

Lumbroso et al., "A Preliminary Study of the Adsorption and Release of Preservatives by Contact Lenses and Collagen Shields," *CLAO Journal*, vol. 22(1), pp. 61–63 (1996).

Minno et al., "Quantitative Analysis of Protein Deposits on Hydrophilic Soft Contact Lenses: 1. Comparison to Visual Methods of Analysis. II. Deposit Variation among FDA Lens Material Groups," *Optometry and Vis. Science*, vol. 68(11), pp. 865–872.

Prager et al., "Radiochemical studies on contact lens soilation, I. Lens uptake of 14C–lysozyme from simple and complex artifical tear solutions," J. of Biomedical Materials Research, vol. 36, pp. 119–124 (1997).

Iwasaki et al., "Absorption of Topical Disodium Cromoglycate and its Preservatives by Soft Contact Lenses," *CLAO Journal*, vol. 14(3), pp. 155–158 (1988).

Jain, "Drug delivery through soft contact lenses," *Britich J. of Ophthalmology*, vol. 72, pp. 150–154 (1988).

Keith et al., "A novel procedure for the extraction of protein deposits from soft hydrophilic contact lenses for analysis," *Current Eye Research*, vol. 16(5), pp. 503–510 (1997).

Brodsky, "Allergic Conjunctivitis and Contact Lenses Experience with Olopatadine Hydrochloride 0.1% Therpay," Abstract presented at "Challenges, Strategies, and Tools to Optimize the Management of Ocular Allergy 2$^{nd}$ International Symposium," Leeds Castle, Kent England, Jun. 22–25, 1999.

Christensen et al., "Five–Minute Removal of Soft Lenses Prevents Most Absorption of a Topical Ophthalmic Solution," *CLAO Journal*, vol. 24(4), pp. 227–231.

Dassanayake et al., "A Laboratory Model to Determine the Uptake and Release of Olopatadine by Soft Contact Lenses," Abstract presented at "Challenges, Strategies, and Tools to Optimize the Management of Ocular Allergy 2$^{nd}$ International Symposium," Leeds Castle, Kent England, Jun. 22–25, 1999.

* cited by examiner

*Primary Examiner*—Thurman K. Page
*Assistant Examiner*—Robert M. Joynes
(74) *Attorney, Agent, or Firm*—Patrick M. Ryan

(57) ABSTRACT

Topically administrable anti-allergy compositions comprising olopatadine and a polymeric quaternary ammonium preservative are suitable for use by patients wearing contact lenses.

19 Claims, No Drawings

OPHTHALMIC ANTI-ALLERGY COMPOSITIONS SUITABLE FOR USE WITH CONTACT LENSES

This application claims priority to co-pending U.S. Provisional Application, U.S. Ser. No. 60/177,804 filed Jan. 25, 2000.

BACKGROUND OF THE INVENTION

The present invention relates generally to ophthalmic anti-allergy compositions. In particular, the present invention relates to topical anti-allergy compositions that can be safely applied by a patient wearing contact lenses.

Ophthalmic formulations generally contain one or more active compounds along with excipients such as surfactants, comforting agents, complexing agents, stabilizers, buffering systems, chelating agents, viscosity agents or gelling polymers and anti-oxidants. Ophthalmic formulations which are intended for multidose use require a preservative. Benzalkonium chloride ("BAC") is the most widely used ophthalmic preservative.

Topically administrable multidose ophthalmic products are generally not suitable for use with contact lenses because the active or the preservative may bind to or accumulate in the contact lenses, causing irritation or toxic effects.

Olopatadine is a known anti-allergy drug. See U.S. Pat. No. 5,641,805 (Yanni, et al.). PATANOL® brand of olopatadine hydrochloride ophthalmic solution is marketed as a topical anti-allergy composition. Emedastine is a known anti-histamine drug. EMADINE® brand of emedastine difumarate solution is marketed as a topical anti-allergy composition. Like other topically administrable anti-allergy products, these compositions are preserved with BAC. BAC is known to bind to or accumulate in contact lenses. Thus, like other topically administrable ophthalmic pharmaceutical products containing BAC, PATANOL® brand of olopatadine hydrochloride ophthalmic solution and EMADINE® brand of emedastine difumarate ophthalmic solution contain in their labelling information precautionary instructions to remove contact lenses before use and to wait ten minutes after administering the product before replacing the lenses. The dosing regimen for anti-allergy products typically calls for two to four applications a day, making it inconvenient for contact lens wearers to treat ophthalmic allergy symptoms.

Polyquaternium-1, which is used under the trade name Polyquad® is one preservative known to be compatible with contact lenses. Polyquaternium-1 and other polymeric quaternary ammonium compounds are used as disinfectants and preservatives in contact lens care and artificial tear solutions. See, for example, U.S. Pat. Nos. 5,037,647; 4,525,346; and 4,407,791. The currently marketed Opti-Free® brand of contact lens care products, including multi-purpose solutions and cleaning solutions, contains polyquaternium-1 as a disinfectant and preservative.

In addition to contact lens care products, polyquaternium-1 can also be used as a preservative in certain topically administrable ophthalmic drug products. U.S. Pat. No. 5,603,929 discloses the use of polyquaternium-1 in combination with boric acid to preserve topically administrable ophthalmic compositions of acidic drugs, such as non-steroidal anti-inflammatory drugs. Although the '929 patent defines suitable ophthalmic drug compounds for use with the polyquaternium-1 and boric acid preservative system to include ophthalmically acceptable salts, amides, esters and prodrugs of the many types of acidic drugs, it does not mention anti-allergy drugs or olopatadine in particular. See Col. 3, lines 12–30 of the '929 patent.

SUMMARY OF THE INVENTION

It has now been discovered that compositions of olopatadine and emedastine that comprise polyquaternium-1 as a preservative are suitable for use with contact lenses. The present invention relates to multi-dose, topically administrable compositions of olopatadine and emedastine containing a polymeric quaternary ammonium compound, such as polyquaternium-1, as a preservative. The compositions of the present invention do not contain BAC.

The present invention also relates to a method for treating or controlling ocular allergies in patients wearing contact lenses which comprises topically administering a composition comprising olopatadine or emedastine and a polymeric quaternary ammonium compound as a preservative, where the composition is applied without removing the contact lenses.

DETAILED DESCRIPTION OF THE INVENTION

Olopatadine is (Z)-11-(3-dimethylaminopropylidene)-6,11-dihydrodibenz[b,e]-oxepin-2-acetic acid. Olopatadine can be made using the methods disclosed in U.S. Pat. No. 5,116,863, the entire contents of which are hereby incorporated by reference. The concentration of olopatadine in the compositions of the present invention will range from about 0.0001 to 5% (w/v), preferably from about 0.001 to 0.25% (w/v), and most preferably from about 0.1 to 0.25% (w/v), based on the sterilized purified water. The olopatadine ingredient may be present in the form of a pharmaceutically acceptable salt. Unless indicated otherwise, "olopatadine" as used herein refers to both olopatadine and its pharmaceutically acceptable salts. The most preferred form of olopatadine is olopatadine hydrochloride. The most preferred concentration of olopatadine hydrochloride is from about 0.111 to 0.222% (w/v), which is equivalent to 0.1 to 0.2% (w/v) olopatadine.

Emedastine's chemical name is 1-(2-ethoxyethyl)-2-(4-methyl-1-homopiper-azinyl)-benzimidazole. The ophthalmic use of emedastine is disclosed in U.S. Pat. No. 5,441,958. Emedastine can be made using the methods disclosed in U.S. Pat. No. 4,430,343, the entire contents of which are hereby incorporated by reference. The concentration of emedastine in the compositions of the present invention will range from about 0.0001 to 1% (w/v), preferably from about 0.005 to 0.1% (w/v), and most preferably about 0.05% (w/v). The emedastine ingredient may be present in the form of a pharmaceutically acceptable salt. Unless indicated otherwise, "emedastine" as used herein refers to both emedastine and its pharmaceutically acceptable salts. The most preferred form of emedastine is emedastine difumarate. The most preferred concentration of emedastine difumarate is about 0.0884% (w/v), which is equivalent to 0.05% (w/v) emedastine.

In addition to olopatadine or emedastine, or a pharmaceutically acceptable salt thereof, the compositions of the present invention contain a polymeric quaternary ammonium compound as a preservative. The polymeric quaternary ammonium compounds useful in the compositions of the present invention are those which have an antimicrobial effect and which are ophthalmically acceptable. Preferred compounds of this type are described in U.S. Pat. Nos. 3,931,319; 4,027,020; 4,407,791; 4,525,346; 4,836,986;

5,037,647 and 5,300,287; and PCT application WO 91/09523 (Dziabo et al.). The most preferred polymeric ammonium compound is polyquaternium-1, otherwise known as Polyquad® or Onamer M®, with a number average molecular weight between 2,000 to 30,000. Preferably, the number average molecular weight is between 3,000 to 14,000.

The polymeric quaternary ammonium compounds are generally used in the compositions of the present invention in an amount from about 0.00001 to about 3% (w/v), preferably from about 0.001 to about 0.1% (w/v). Most preferably, the compositions of the present invention contain from about 0.001 to about 0.05% (w/v) of polymeric quaternary ammonium compounds.

It may be necessary or desirable to add boric acid to the compositions to achieve desired levels of preservative efficacy. See U.S. Pat. No. 5,603,929, the entire contents of which are hereby incorporated by reference. The boric acid suitable for use in the compositions of the present invention includes not only boric acid, but also its ophthalmically acceptable acid addition salts, as well as borate-polyol complexes of the type described in U.S. Pat. No. 5,342,620 (Chowhan). If present, the amount of boric acid will generally range from about 0.3 to about 5.0% (w/v).

The compositions of the present invention should have an ophthalmically acceptable tonicity, such as 260–320 mOsm/kg, and an ophthalmically acceptable pH, such as pH 5–8, and preferably pH 6.8–7.6. The topically administrable, multi-dose compositions of the present invention optionally comprise other excipients, such as tonicity adjusting agents, buffering agents, chelating agents, and pH adjusting agents. For example, sodium chloride, mannitol, or the like may be used as the isotonic agent; sodium hydrogenphosphate, sodium dihydrogenphosphate, p-hydroxybenzoic acid ester, boric acid or the like as the buffering agent; sodium edetate or the like as the chelating agent or stabilizer; and sodium hydroxide, hydrochloric acid or the like as the pH adjusting agent.

The compositions of the present invention may also include viscosity modifying agents such as: cellulosic ethers, such as, hydroxypropyl methyl cellulose (HPMC), hydroxyethyl cellulose (HEC), ethyl hydroxyethyl cellulose, hydroxypropyl cellulose, methyl cellulose, and carboxymethyl cellulose; carbomers (e.g. Carbopol®; polyvinyl alcohol; polyvinyl pyrrolidone; alginates; carrageenans; and guar, karaya, agarose, locust bean, and xanthan gums.

The following examples are presented to illustrate further various aspects of the present invention, but are not intended to limit the scope of the invention in any respect.

EXAMPLE 1

| Ingredient | Formulation (% w/v) | |
|---|---|---|
| | A | B |
| Olopatadine Hydrochloride | 0.111 or 0.222 | 0.111 or 0.222 |
| NaCl | q.s. to 260–320 mOsm/kg | 0.3 |
| Polyethylene Glycol (400) | 2.0 | 2.0 |
| Polyquaternium-1 | 0.001–0.15 | 0.005 |
| Dibasic sodium phosphate (anhydrous) | 0.5 | 0.5 |
| HCl/NaOH | q.s. to pH 6.8–7.2 | q.s. to pH 7 |
| Purified Water | q.s. to 100% | q.s. to 100% |

EXAMPLE 2

| Ingredient | Formulation (% w/v) | |
|---|---|---|
| | C | D |
| Emedastine difumarate | 0.0884 | 0.0884 |
| NaCl | q.s. to 260–320 mOsm/kg | 0.68 |
| Hydroxypropyl methylcellulose (2910) | 0.25 | 0.25 |
| Tromethamine | 0.5 | 0.5 |
| Polyquaternium-1 | 0.001–0.15 | 0.005 |
| Dibasic Sodium Phosphate (Anhydrous) | 0.5 | 0.5 |
| HCl/NaOH | q.s. to pH 7.2–7.6 | q.s. to pH 7.4 |
| Purified Water | q.s. to 100% | q.s. to 100% |

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A topically administrable, multi-dose anti-allergy composition suitable for use by patients wearing contact lenses, wherein the composition comprises an anti-allergy effective amount of a drug selected from the group consisting of olopatadine and emedastine; and an ophthalmically acceptable polymeric quaternary ammonium compound as a preservative, provided that the composition does not contain benzalkonium chloride.

2. The composition of claim 1 wherein the drug is olopatadine and the anti-allergy effective amount of olopatadine is from about 0.0001 to 5% (w/v).

3. The composition of claim 2 wherein the anti-allergy effective amount of olopatadine is from about 0.001 to 0.25% (w/v).

4. The composition of claim 3 wherein the olopatadine is olopatadine hydrochloride and the anti-allergy effective amount of olopatadine is from about 0.1–0.25% (w/v).

5. The composition of claim 1 wherein the drug is emedastine and the anti-allergy effective amount of emedastine is from about 0.0001 to 1% (w/v).

6. The composition of claim 5 wherein the anti-allergy effective amount of emedastine is from about 0.005 to 0.1% (w/v).

7. The composition of claim 5 wherein the emedastine is emedastine difumarate and the anti-allergy effective amount of emedastine is about 0.0884% (w/v).

8. The composition of claim 1 wherein the polymeric quaternary ammonium compound is polyquaternium-1.

9. The composition of claim 8 wherein the polymeric quaternary ammonium compound is present in an amount from about 0.00001 to about 3% (w/v).

10. The composition of claim 9 wherein the polymeric quaternary ammonium compound is present in an amount from about 0.001 to about 0.1% (w/v).

11. The composition of claim 1 wherein the composition further comprises one or more ingredients selected from the group consisting of tonicity adjusting agents; buffering agents; chelating agents; pH adjusting agents; and viscosity modifying agents.

12. A method for treating or controlling ocular allergies in patients wearing contact lenses which comprises topically administering a composition comprising an anti-allergy effective amount of a drug selected from the group consisting of olopatadine and emedastine; and a polymeric quaternary ammonium compound as a preservative, wherein the composition is applied without removing the contact lenses and the composition does not contain benzalkonium chloride.

13. The method of claim 12 wherein the drug is olopatadine and the anti-allergy effective amount of olopatadine is from about 0.0001 to 5% (w/v).

14. The method of claim 13 wherein the olopatadine is olopatadine hydrochloride and the anti-allergy effective amount of olopatadine is from about 0.1 to 0.25% (w/v).

15. The method of claim 12 wherein the drug is emedastine and the anti-allergy effective amount of emedastine is from about 0.005 to 0.1% (w/v).

16. The method of claim 15 wherein the emedastine is emedastine difumarate and the anti-allergy effective amount of emedastine is about 0.0884% (w/v).

17. The method of claim 12 wherein the polymeric quaternary ammonium compound is polyquaternium-1.

18. The method of claim 17 wherein the polymeric quaternary ammonium compound is present in an amount from about 0.00001 to about 3% (w/v).

19. The method of claim 12 wherein the composition further comprises one or more ingredients selected from the group consisting of tonicity adjusting agents; buffering agents; chelating agents; pH adjusting agents; and viscosity modifying agents.

* * * * *